United States Patent
Durnell et al.

(10) Patent No.: US 9,271,648 B2
(45) Date of Patent: Mar. 1, 2016

(54) EYE TRACKING APPARATUS

(75) Inventors: Laurence Durnell, Alton (GB); Donald Nigel Jarrett, Keynsham (GB)

(73) Assignee: QINETIQ LIMITED, Hampshire (GB)

( * ) Notice: Subject to any disclaimer, the term of this patent is extended or adjusted under 35 U.S.C. 154(b) by 658 days.

(21) Appl. No.: 13/583,835

(22) PCT Filed: Mar. 11, 2011

(86) PCT No.: PCT/GB2011/000340
§ 371 (c)(1), (2), (4) Date: Sep. 10, 2012

(87) PCT Pub. No.: WO2011/114092
PCT Pub. Date: Sep. 22, 2011

(65) Prior Publication Data
US 2013/0010097 A1    Jan. 10, 2013

(30) Foreign Application Priority Data
Mar. 16, 2010   (GB) .................................. 1004346.1

(51) Int. Cl.
  *H04N 7/18*    (2006.01)
  *A61B 3/113*   (2006.01)
  *A61B 5/00*    (2006.01)
  *G06F 3/01*    (2006.01)

(52) U.S. Cl.
  CPC ............... *A61B 3/113* (2013.01); *A61B 5/6814* (2013.01); *G06F 3/013* (2013.01)

(58) Field of Classification Search
  CPC ......... H04N 7/18; H04N 5/225; A61B 3/113; A61B 5/6814; G06F 3/013
  USPC .............. 348/77, 78, 169; 382/117, 103, 115, 382/118
  See application file for complete search history.

(56) References Cited

U.S. PATENT DOCUMENTS

| | | | |
|---|---|---|---|
| 4,852,988 A | | 8/1989 | Velez et al. |
| 5,016,282 A | * | 5/1991 | Tomono et al. ................ 382/117 |
| 7,130,447 B2 | * | 10/2006 | Aughey et al. ................ 382/103 |

(Continued)

FOREIGN PATENT DOCUMENTS

| | | |
|---|---|---|
| EP | 0 125 808 A2 | 11/1984 |
| WO | 01/49167 A1 | 7/2001 |

(Continued)

OTHER PUBLICATIONS

Jul. 13, 2010 Combined Search Report and Examination Report issued in British Patent Application No. 1004346.1.

(Continued)

*Primary Examiner* — Trang U Tran
(74) *Attorney, Agent, or Firm* — Oliff PLC (57) ABSTRACT

An eye tracking apparatus for monitoring a user's eye, for use in conjunction with secondary optical apparatus such as binoculars or night vision goggles. An optical assembly is adapted directly to image the eye from within the user's field of vision, and relay the image to a sensing element, which can be located outside the field of vision. Additionally the scene is imaged, also optionally from within the user's field of vision, which allows for scene imaging through the secondary optical apparatus. The optical assembly typically extends across the eyepiece of for example binoculars, and can be provided in a small form factor so as to interfere minimally with the view through the eyepiece. Both eye image and scene image can be relayed through the optical assembly, resulting in further space efficiencies.

20 Claims, 4 Drawing Sheets

(56) References Cited

U.S. PATENT DOCUMENTS

| | | | |
|---|---|---|---|
| 7,306,337 B2 * | 12/2007 | Ji et al. | 351/209 |
| 7,391,887 B2 * | 6/2008 | Durnell | 382/117 |
| 7,401,920 B1 * | 7/2008 | Kranz et al. | 351/210 |
| 2003/0156257 A1 | 8/2003 | Levola | |
| 2007/0201847 A1 | 8/2007 | Lei | |
| 2010/0053555 A1 | 3/2010 | Enriquez et al. | |

FOREIGN PATENT DOCUMENTS

| | | |
|---|---|---|
| WO | WO 03/017203 A1 | 2/2003 |
| WO | WO 2005/052718 A2 | 6/2005 |
| WO | WO 2007/043954 A1 | 4/2007 |
| WO | WO 2009/043927 A1 | 4/2009 |

OTHER PUBLICATIONS

Jun. 1, 2011 Written Opinion of the International Searching Authority issued in International Patent Application No. PCT/GB2011/000340.

Jun. 1, 2011 International Search Report issued in International Patent Application No. PCT/GB2011/000340.

May 8, 2014 Office Action issued in European Patent Application No. 11 710 813.4.

* cited by examiner

EYE TRACKING APPARATUS

The present invention relates an eye tracking apparatus and to a method of monitoring the movement of a user's eyes. Without limitation, the invention relates to an eye tracking apparatus capable of operating in conjunction with a secondary optical apparatus.

Conventional eye tracking apparatuses typically use a semi-transmissive optical combiner disposed in a user's field of vision to capture images of the user's eye while allowing the user a substantially unimpeded view of the scene to be observed through the combiner. However, such eye tracking apparatuses suffer from unwanted reflections from the ambient surroundings on the optical combiner, and reduced transmission of light from the scene. Accurate determination of eye position can be difficult under such circumstances.

Conventional eye tracking apparatuses are not typically intended to operate in conjunction with secondary optical apparatuses, e.g. simultaneously to track the position of a user's eye image when viewing a scene through a secondary optical apparatus such as a microscope, a telescope, or electro-optic goggles. Such an application presents difficulties for conventional eye tracking apparatuses because of the disparate focus requirements for the eye and the scene as viewed through the secondary optical apparatus. Difficulties may also arise in providing eye tracking while maintaining correct or desired eye relief.

It is an object of the invention to provide an eye tracking apparatus which mitigates at least one disadvantages of conventional devices.

According to a first aspect of the present invention, there is now proposed an eye tracking apparatus for monitoring the movement of a user's eye, the apparatus comprising:
  a) an optical assembly comprising an eye viewing element adapted to directly image a user's eye from within the user's field of vision, and an eye imaging sensor adapted to receive an image of the user's eye from said eye viewing element and provide an output indicative of the user's point of regard in the user's field of vision, said optical assembly including a first imaging path between said eye viewing element and said eye imaging sensor;
  b) a scene viewing element adapted to image a scene being observed by the user's eye and a scene imaging sensor adapted to receive an image of the scene from said scene viewing element via a second imaging path.

The eye viewing element directly images the user's eye by intercepting electromagnetic radiation reflected from the user's eye.

Apparatus according to this aspect of the invention offers the advantage that the optical assembly can image a users eye from within the user's field of vision and relay the image along the first imaging path to an eye imaging sensor which can be located remotely from the user's eye, and desirably from the user's field of vision. The first imaging path may be longer than or equal to 30 mm, 50 mm or even 70 mm in embodiments. Thus only the eye viewing element need to occupy the user's field of vision and the eye imaging sensor can be located to one side, or above or below the field of vision so as to cause minimum disruption or inconvenience to the user, and to impede their view of a scene minimally. The eye viewing element is preferably a reflector, for example a plane mirror, and the eye viewing element may be substantially opaque to radiation from a scene directed towards the user's eye. Desirably the eye viewing element is less than or equal to 10 mm, 5 mm or even 3 mm in diameter, or equivalent external dimension. The first imaging path may be angled or folded, for example by one or more fold mirrors, in order that the eye imaging sensor can be conveniently located.

The optical assembly in typical embodiments will generally be elongate and may include a structural housing or casing. The optical assembly can advantageously be arranged to have a small thickness or profile relative to its length in the direction of elongation. Since, in addition to the eye viewing element, some or all of the first imaging path may lie within the user's field of vision, any housing or structural element present will desirably be minimally disruptive to the user's field of view.

From the above it can be seen that in many embodiments the invention provides means for taking light reflected from a user's eye, from within the field of vision of that user, and steering that light to a sensor to image or record the user's point of regard. At the same time sufficient light from the scene should be allowed to reach the user's eye to allow the user to view the scene. In embodiments of the present invention this is achieved by providing an optical assembly having an appropriate form factor. In other words, spatially, the optical assembly occupies only a small proportion of the field of view of the user, with the remainder of the spatially unoccupied proportion of the field of view being unaffected and passing substantially 100% of incident visible light to the user's eye. This is in contrast to any approach which relies on light from the scene to passing through, for example, a semi transmissive element, allowing a certain percentage (eg 85%) of visible light to pass to the user's eye.

In a preferred embodiment, the optical assembly includes one or more relay lenses along said first optical path, adapted to provide a conjugate image of a user's eye at a plane intermediate the eye viewing element and the eye imaging sensor. This provides the advantage of elongating the first optical path thereby minimising disruption to the user as indicated above.

The relay lenses are beneficial in that they cooperate to extend the optical path length between the viewing elements and the image sensors which enables the image sensors to be positioned substantially out of the user's field of vision. Relay lenses are employed in the present eye tracking apparatus in preference to using a long focal length eye objective lens. This is because of the desire to keep optical components within the user's field of vision as small as possible and the need to efficiently capture radiation reflected from the user's eye. By way of explanation, a long focal length eye objective lens would exhibit a high f-number (i.e. it would be a 'slow' lens) and would therefore be less able to pass sufficient light from the user's eye to from a useable image thereof. A long focal length eye objective lens would be able to view only a small area of the user's eye and would be less effective at capturing a sufficiently wide view of the user's eye to accommodate for head movement with respect to the eye tracking apparatus.

In embodiments of the invention, the optical assembly includes an optical combiner arranged to align at least a portion of the first and second imaging paths coaxially along a common optical path. It will be advantageous in many embodiments for the scene viewing element to be arranged in close proximity to the eye viewing element, preferably at a separation of less than or equal to 20 mm or 10 mm of the eye viewing element, optionally within 10-20 mm of the eye viewing element, and possibly within the field of vision of the user. The scene viewing element may therefore be included within the optical assembly in embodiments. This is beneficial in reducing parallax errors which may be minimised by substantially collocating the scene viewing element with the user's eye. This is especially true if the apparatus is adapted to be used in conjunction with a secondary optical apparatus, e.g. binoculars or the like, and it is desired to capture an image of the scene through the secondary optical apparatus. It remains desirable however for the scene imaging sensor to be located remotely from the scene viewing element, and these advantages can ingeniously be accommodated in embodiments in which the first and second imaging paths are at least in part coaxial.

In a preferred embodiment, the eye imaging sensor is adapted to image an object plane proximal to the eye viewing element and the scene imaging sensor is adapted to image an object plane distal to the scene viewing element, preferably at infinity. The ability of embodiments of the invention simultaneously to image an object plane at close range (i.e. the user's eye at a distance of approximately 20-50 mm) and an object plane at long range (i.e. the scene or an image of the scene displayed so as to appear substantially at infinity) is particularly advantageous. Even more advantageous are embodiments in which both eye and scene image are passed, at least in part, along a common imaging path to imaging sensors located remotely to the viewing elements, and in which viewing elements and optionally a portion of the imaging path are adapted to be located in a user's field of view, but can be sufficiently compact to as not obscure a significant portion of the user's field of view. Embodiments, for example, occupy less than or equal to 15%, or even 10% or 5% of a user's field of view in use. Components of this aspect of the invention which occupy the user's field of view in use may have a viewed area of less than or equal to 250 mm$^2$ or even 100 mm$^2$.

Conveniently, the eye viewing element is disposed in use within the user's lower field of vision in a region substantially 10-20 degrees below the user's straight ahead gaze, preferably 12-18 degrees below the user's straight ahead gaze.

Without limitation, the output from the eye imaging sensor indicative of the user's point of regard in the user's field of vision may be an image of the user's eye. The image may include a detectable reference point caused by reflection from the surface of the eye of a light source in certain embodiments.

The eye tracking apparatus may further include a video image recorder for recording the output from the eye imaging sensor indicative of the user's point of regard in the user's field of vision and an output from the scene imaging sensor. Preferably, the video image recorder is arranged to alternately record an output from the eye imaging sensor and the output from the scene imaging sensor.

In another embodiment, the eye tracking apparatus further comprises a processor adapted to determine the user's absolute point of regard in the user's field of vision.

The eye tracking apparatus may also comprise a display for displaying the user's absolute point of regard, with respect to an image of the scene being observed by the user's eye.

According to a further aspect of the present invention, there is now proposed an optical apparatus comprising one of spectacles, goggles, night-vision goggles, virtual reality goggles, augmented reality goggles, a microscope, a telescope, an optical and/or telescopic sight, binoculars and a head-mounted display arranged in combination with an eye tracking apparatus according to the first aspect of the present invention.

The optical apparatus of embodiments of such aspects will typically comprise an eyepiece, and the optical assembly preferably extends at least partially across the front of said eyepiece. The optical apparatus preferably obscures less than or equal to 15%, 10% or 5% of the optically transmissive area of the eyepiece.

Therefore embodiments provide for secondary optical apparatus including an eyepiece, or ocular lens, with the optical assembly extending partially across the eyepiece or lens, to lie between the eyepiece or lens and the user's eye in use, while sill allowing desired eye relief, which may be as little as 25 mm in examples.

Night-vision goggles incorporating an eye tracking capability allow the user of said goggles to be observed and provide an accurate assessment of the user's behaviours. For example, trials have demonstrated that flight safety at night can be improved by the use of display night-vision goggle symbology. This symbology provides the pilot with enhanced situational awareness and navigation and landing cues. The present eye tracking apparatus is of great benefit during design and procurement of such symbology.

The present eye tracking apparatus may also be applied to night driving in land vehicles. For example, the use of eye tracking equipped night-vision goggles by a novice driver allows the driving instructor to see exactly what information the novice driver is using and so would speed up training by allowing problems to be identified early. It would be possible to automate some aspects, e.g. detecting instrument or symbology scans or extended fixation on one area, so that the novice driver can be alerted immediately.

Furthermore, knowledge of how experts use night-vision goggles for night flying and night driving will make training more efficient and eye tracking can allow the students' performance to be evaluated more effectively.

Similarly, in the medical field, knowledge of how analysts assess biopsy samples for anomalies can be used to identify best practices and can enable trainee analysts' performance to be effectively evaluated.

According to a further aspect of the present invention, there is now proposed a method of monitoring the movement of a user's eye comprising the steps of:

(a) capturing an image of the user's eye from a first position within the user's field of vision and relaying said image along a first optical path to a remote eye imaging sensor arranged out of the user's field of vision, (b) capturing an image of a scene being observed by the user's eye from a second position within the user's field of vision and relaying said image along substantially the same first optical path to a remote scene imaging sensor arranged out of the user's field of vision, wherein the images of the user's eye and scene are captured at substantially the same time.

Preferably, the method comprises the additional step of:

(c) providing an output indicative of the user's point of regard in the user's field of vision.

Without limitation, the output indicative of the user's point of regard in the user's field of vision is typically an image of the user's eye.

The invention extends to methods, apparatus and/or use substantially as herein described with reference to the accompanying drawings.

Any feature in one aspect of the invention may be applied to other aspects of the invention, in any appropriate combination. In particular, method aspects may be applied to apparatus aspects, and vice versa.

Preferred features of the present invention will now be described, purely by way of example, with reference to the accompanying drawings, in which.

Figure 1:
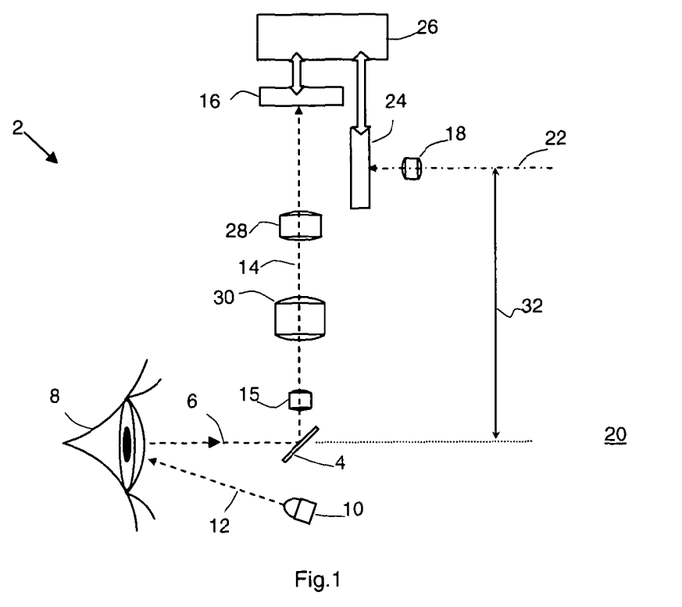
FIG. 1 shows a schematic cross sectional view of an eye tracking apparatus according to one embodiment of the present invention comprising an optical assembly for capturing an image of the user's eye and for relaying said image to a remote eye imaging sensor.

Referring now to the drawings wherein like reference numerals identify corresponding or similar elements throughout the several views, FIG. 1 shows an eye tracking apparatus 2 according to a first embodiment of the present invention comprising a eye viewing element 4 positioned within a user's field of vision, said eye viewing element 4 being arranged to intercept electromagnetic radiation 6 reflected from the user's eye 8. The eye tracking apparatus 2 also comprises an illumination source comprising at least one infrared light emitting diode (IR LED) 10 arranged to illuminate the user's eye 8 along an illumination path 12 with electromagnetic radiation having a wavelength in the infrared spectrum. Some of the infrared radiation illuminating the user's eye 8 produces at least one detectable bright reference point thereon caused by specular reflection from the anterior surface of the user's eye 8. The bright reference point(s) may be used to determine the user's point of regard in the scene.

The eye viewing element 4 is arranged to receive the infrared radiation 6 reflected from the user's eye 8 and relays said reflected radiation 6 along a first imaging path 14 to an eye imaging sensor 16 arranged remotely to the eye viewing element 4 and in optical communication therewith along the first imaging path 14. The eye viewing element 4 of FIG. 1 comprises a reflector angled with respect to user's eye 8 so as to relay the radiation reflected there-from along the first imaging path 14 via eye objective lens 15. The reflector is partially reflective, optionally substantially reflective, to electromagnetic radiation incident thereon.

Optimally, the eye viewing element 4 is disposed in use within the user's lower field of vision in a region substantially 10-20 degrees below the user's straight ahead gaze. The eye imaging sensor 16 is configured to provide an output, typically an image of the user's eye, indicative of the user's point of regard in the user's field of vision.

Although the eye viewing element 4 is positioned within a user's field of vision, said eye viewing element 4 is small in size (for example, without limitation, substantially 3-5 mm diameter) and hence unobtrusive to the user's the eye 8, even in the case where the eye viewing element 4 is a plane mirror. This is particularly true for applications involving binocular vision where a single eye tracking apparatus 2 is used to monitor only one of the user's eye's, the user's other eye having an unimpeded view of the scene 20.

Applicant's research has established that in such cases the user compensates for the obstruction caused by the eye viewing element 4 by giving increased emphasis to the view of the scene from the unimpeded eye. Accordingly, the eye viewing element 4 merely appears as a darker area within the user's field of vision.

As mentioned above, the small size of the eye viewing element 4 enables said element to be positioned within a user's field of vision, however the eye imaging sensor 16 is too large and obtrusive to be located within the user's field of vision and hence the eye tracking apparatus 2 comprises relay lenses 28, 30 which extend the first optical path 14 and allow the eye imaging sensor 16 to be located remotely to the eye viewing element 4. The relay lenses 28, 30 image the user's eye from a conjugate image at an intermediate plane between relay lens 30 and the eye objective lens 15 onto the eye imaging sensor 16.

Relay lenses 28, 30 are employed in the present eye tracking apparatus 2 in preference to having a longer focal length eye objective lens 15. This is because of the requirement to keep optical components within the user's field of vision as small as possible, the need to efficiently capture radiation 6 reflected from the user's eye and the need to capture a large image area of the user's eye to allow for head movement with respect to the eye tracking apparatus.

Accordingly, obscuration of the user's field of vision is minimised by combining the eye viewing element 4, the eye objective lens 15 and relay lenses 28, 30 within a common optical assembly which relays the image of the user's eye 8 to the remote eye imaging sensor 16.

The eye tracking apparatus 2 also comprises a scene viewing element 18 adapted to intercept electromagnetic radiation received from a scene 20 being observed by the user's eye 8 and to relay said received radiation along a second imaging path 22 to a scene imaging sensor 24. The scene viewing element 18 of FIG. 1 comprises a scene objective lens arranged with respect to scene 20 so as to relay the radiation reflected there from along the second imaging path 22.

Outputs from the eye imaging sensor 16 and the scene imaging sensor 24 are passed to a processor 26 for further conditioning and processing. The output from the processor 26 comprises images of the user's eye and the scene being observed by the user's eye. Optionally the processor provides an output indicative of the user's absolute point of regard in the scene.

The configuration of FIG. 1 is beneficial in that the scene imaging element 18 and scene imaging sensor 24 are arranged out of the user's field of vision, However, correction may be required for the parallax offset 32 between the path along which the user's eye 8 and the scene imaging sensor 24 respectively observe the scene 20. The parallax error is mitigated by the embodiment of FIG. 2.

Figure 2:
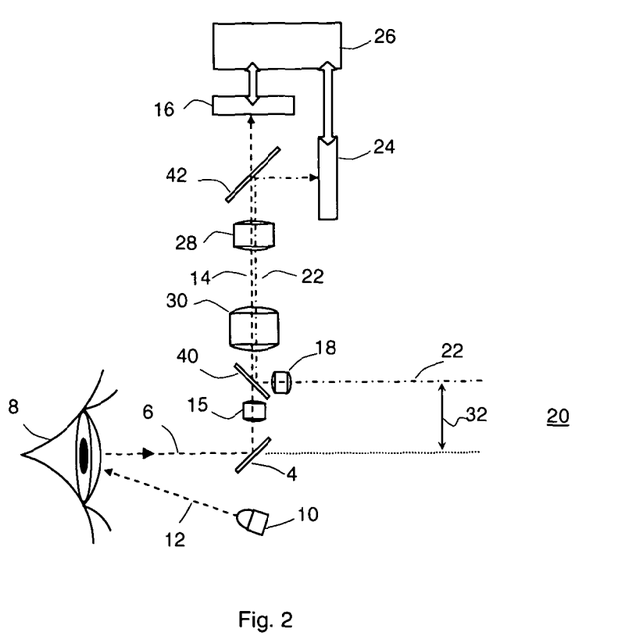
FIG. 2 shows a schematic cross sectional view of an eye tracking apparatus according to another embodiment of the present invention comprising an optical assembly for capturing an image of the user's eye and an image of the scene being observed, and for relaying said images to a remote eye imaging sensor.

Referring to FIG. 2, in an alternative embodiment of the present invention the scene viewing element 18 is disposed within the user's field of vision and the scene imaging sensor 24 is located remotely there-from and out of the user's field of vision. In this embodiment, an optical combiner 40 is employed to intercept electromagnetic radiation received from the scene objective lens 18 and to route said received radiation along the second imaging path 22 through relay lenses 28 and 30 and an optical splitter 42 to the scene imaging sensor 24.

In this configuration, at least a portion of the first and second optical paths 14, 22 are aligned coaxially along a common optical path within the optical assembly. This is beneficial in that the physical size of the optical assembly is minimised because the relay lenses 28, 30 are common to both the first and second optical paths 14, 22, thereby obviating duplication of optical elements.

By way of brief explanation of the way in which the first and second optical paths 14, 22 are combined and subsequently separated within the apparatus 2, the optical combiner 40 comprises a first cold mirror arranged to substantially transmit infrared radiation 6 reflected from the user's eye and arranged to be substantially reflective to visible radiation received from the scene 20. In this manner the first and second optical paths 14, 22 are arranged to be coaxial as they pass through relay lenses 28, 30. Hence, both first and second optical paths are elongated by the relay lenses 28, 30.

Conjugate images of the user's eye 8 and the scene 20 are projected onto a common intermediate plane ahead of relay lens 30 and imaged by relay lenses 28 and 30 onto the eye imaging sensor 16 and the scene imaging sensor 24. Alternatively, the conjugate image of the user's eye 8 is projected onto a first intermediate plane and the conjugate image of the scene 20 is projected onto a different intermediate plane ahead of relay lens 30. Allowance can be made for different locations of conjugate images by repositioning the eye imaging sensor 16 and/or the scene imaging sensor 24.

Optical splitter 42 comprises a second cold mirror arranged to substantially transmit infrared radiation 6 from the user's eye and arranged to be substantially reflective to visible radiation received from the scene 20. In this manner the infrared radiation 6 passes through the optical splitter 42 to the eye imaging sensor 16, whereas visible radiation from the scene 20 is reflected onto the scene imaging sensor 24.

The eye viewing element 4 is arranged in close proximity to the scene viewing element 18 within the optical assembly to minimise parallax offset 32. Optionally, the scene viewing element 18 is substantially collocating with the user's eye.

Accordingly, parallax offset 32 is reduced while keeping obscuration of the user's field of vision to a minimum by combining the eye viewing element 4, the eye objective lens 15, the scene objective lens 18, the optical combiner 40, the optical splitter 42 and relay lenses 28, 30 within a common optical assembly which relays images of both the user's eye 8 and the scene 20 to the remote eye imaging sensor 16 and the remote scene imaging sensor 24 respectively.

Figure 3:
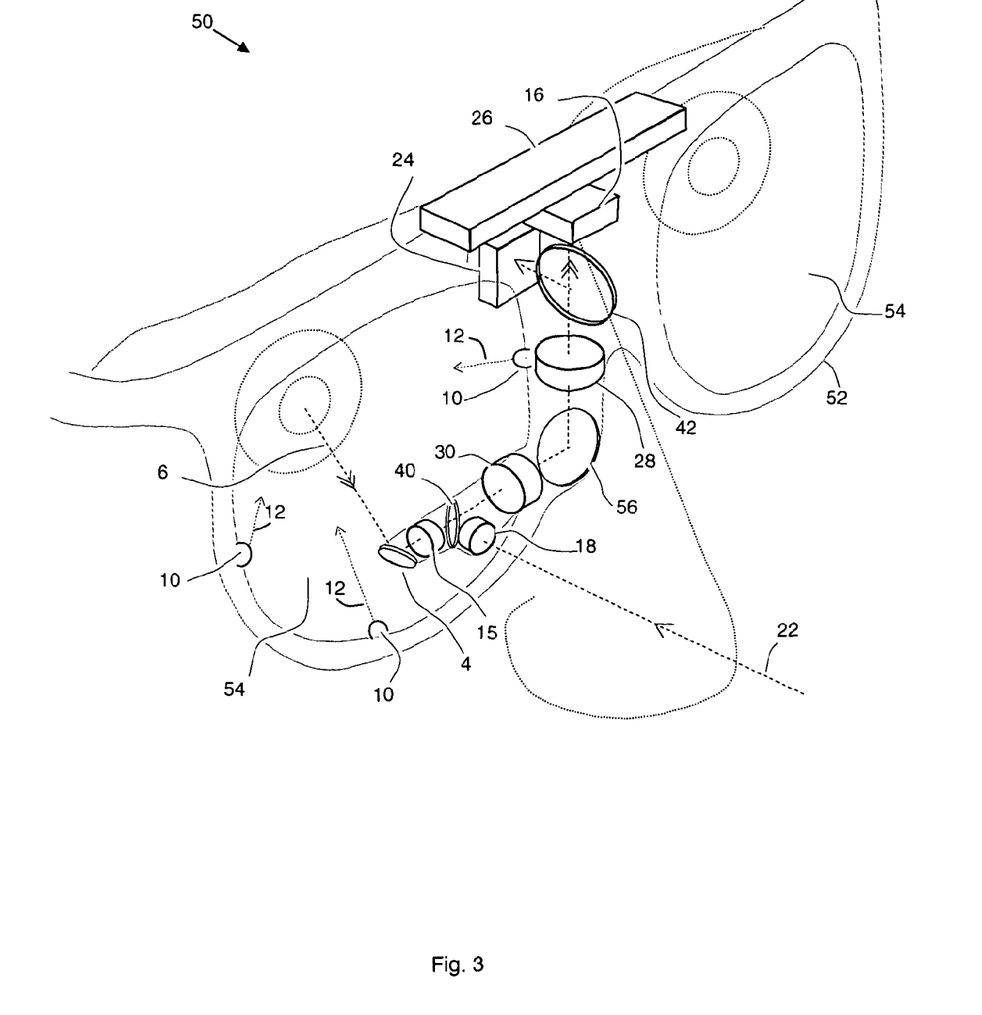
FIG. 3 illustrates a pair of spectacles according to one embodiment of the present invention incorporating the eye tracking apparatus of FIG. 2.

Referring to FIG. 3, the small physical size of the present eye tracking apparatus 2 enables it to be readily incorporated into secondary optical apparatuses for example, without limitation, a pair of spectacles 50. In this embodiment of the invention, the first and second optical axes 14, 22 are folded toward the bridge of spectacles 50 by fold mirror 56 so that images of the user's eye 8 and the scene 20 are routed out of the user's field of vision to remote sensors 16 and 24 located on the upper frame of the spectacles 50.

In an alternative configuration not illustrated in the figures the folded optical assembly extends outward to the side of the spectacle frame so that images of the user's eye 8 and the scene 20 are routed out of the user's field of vision to remote sensors 16 and 24 located on or near to a side arm of the spectacles 50. Alternative configurations will be readily apparent to the skilled person.

The present eye tracking apparatus 2 is also readily incorporated into alternative optical apparatuses, without limitation, into goggles, image intensifier goggle, night-vision goggles, virtual reality goggles, augmented reality goggles, a microscope, a telescope, or a head-mounted display.

Figure 4:
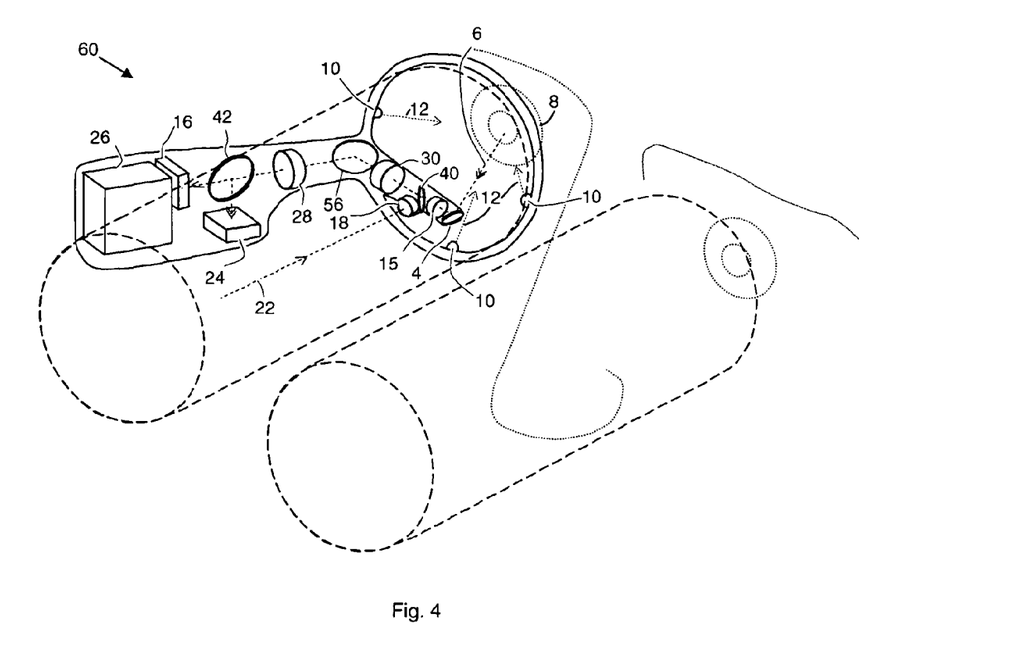
FIG. 4 illustrates a pair of image intensifying goggles according to one embodiment of the present invention incorporating the eye tracking apparatus of FIG. 2.

For example, FIG. 4 illustrates the eye tracking apparatus of FIG. 2 incorporated into a pair of night-vision goggles 60.

In this embodiment of FIG. 4, the eye tracking apparatus is arranged to image the user's eye 8 using the eye viewing element 4 and to image an intensity enhanced output image of the scene 20 produced by the night-vision goggles 60 using the scene viewing element 18. Accordingly, at least part of the optical assembly comprising said viewing elements 4, 18 is interposed, in use, between the user's eye and the optical output of the night-vision goggles.

In this embodiment, the first and second optical axes 14, 22 are folded toward one side of the goggles 60 by fold mirror 56 so that images of the user's eye 8 and the intensity enhanced scene image are routed out of the user's field of vision to remote sensors 16 and 24 located along one side of the night-vision goggles 60. Alternative configurations will be readily apparent to the skilled person.

The ability of the present eye tracking apparatus to focus simultaneously on an object plane at close range (i.e. on the user's eye 8) and on an object plane at long range (i.e. on the scene or on an image of the scene displayed so as to appear substantially at infinity) is particularly beneficial. This enables the present eye tracking apparatus 2 to remain compact while being optically compatible with the above mentioned range of optical apparatuses.

It should be noted that while the optical apparatuses of FIG. 3 and FIG. 4 have been described as having the present eye tracking apparatus therewith, it will be evident to the skilled person that the eye tracking apparatus of FIG. 2 is readily retrofitted to existing optical apparatuses.

The eye tracking apparatus as described in any of foregoing embodiments, optionally includes a video image recorder for recording the output from the eye imaging sensor 16 indicative of the user's point of regard in the user's field of vision and an output from the scene imaging sensor 24. The video image recorder is optionally arranged to alternately record an output from the eye imaging sensor 16 and the output from the scene imaging sensor 24. Alternate outputs may be interleaved as consecutive image frames and/or lines within a video image signal.

Where the eye tracking apparatus is used in conjunction with an active secondary optical apparatus, for example an image intensifier, the output intensity of the infrared LEDs 10 is optionally temporally modulated to reduce stray light 12 from interfering with said secondary optical apparatus. When used in conjunction with the above mentioned video image recorder, the infrared LEDs 10 may be temporally synchronised with video image recorder so as to only provide infrared illumination when the output from the eye imaging sensor 16 is being recorded. Accordingly, the infrared LEDs 10 are optionally extinguished when the output from the scene imaging sensor 24 is being recorded so as to reduce unwanted light pollution of the scene being observed.

Figure 5:
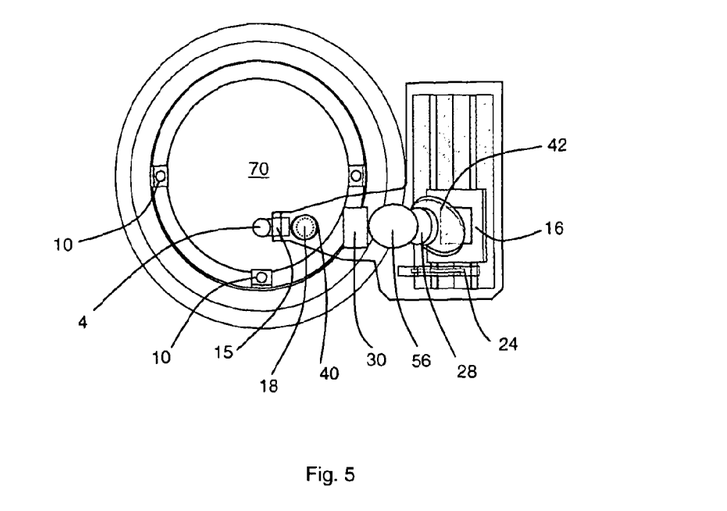
FIG. 5 illustrates a schematic rear elevation view of a night vision goggle eyepiece having the eye tracking apparatus of FIG. 2 integrated therewith.

Referring now to FIG. 5, which shows a user's view of one eye piece of a night vision goggle (for example, the right hand eye piece of binocular night vision goggles), the optical assembly of the present eye tracking apparatus can clearly be seen extending in front of said eyepiece 70 from the outermost periphery of said night vision goggles and obscuring at least part of the optically transmissive area of said eye piece 70.

As can be seen in FIG. 5, the optical assembly comprises an elongate structural housing or casing. The housing is shown partially transparent in the figure to allow the internal components thereof to be seen, however in practice the housing is substantially opaque and therefore obscures part of the user's field of vision through said eyepiece 70. However, the optical assembly is arranged to have a small thickness or profile relative to its length in the direction of elongation so as to be minimally disruptive to the user's field of view.

In this embodiment, the optical assembly of the eye tracking apparatus is located below the user's centre line of vision so that during use the eye viewing element 4 looks up at the user's eye with a look up angle in the range 10-20 degrees.

Figure 6:
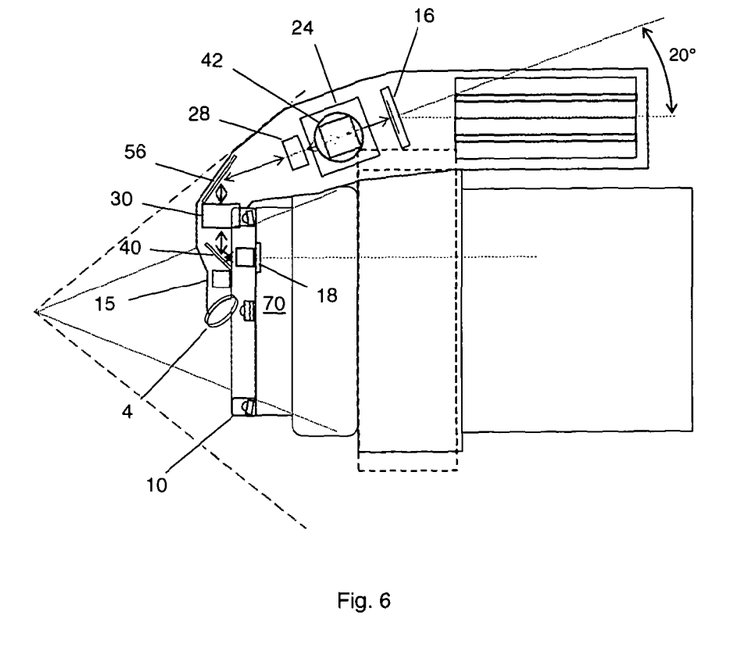
FIG. 6 illustrates a schematic view of the night vision goggle eyepiece of FIG. 5 from below.

FIG. 6 shows a schematic view of the night vision goggle eyepiece of FIG. 5 from below. This figure clearly shows how the optical assembly can image the users eye and the scene image from the night vision goggle eyepiece 70 from within the user's field of vision and relay said images along a common optical path to the eye imaging sensor and scene imaging sensors which are located remotely from the user's eye at the side of the night vision goggles. As indicated in FIG. 6, the first and second optical paths are angled or folded by fold mirror 56 in order that the eye imaging sensor and scene imaging sensor can be conveniently located to the side of the night vision goggles. Thus the eye and scene imaging sensors can be located to one side of the goggles and substantially out of the field of vision so as to cause minimum disruption or inconvenience to the user, and to impede the view of a scene minimally.

Figure 7:
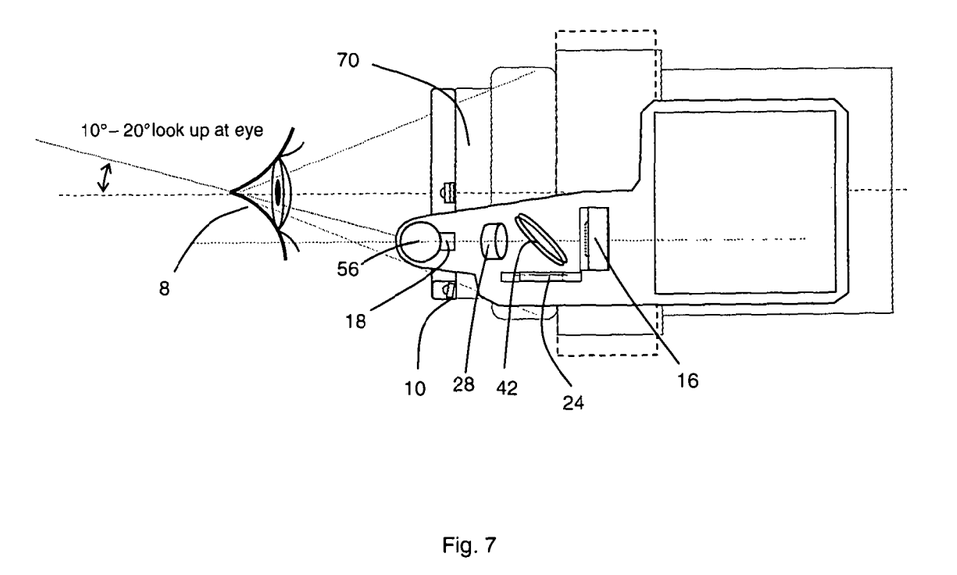
FIG. 7 illustrates a schematic side elevation view of the night vision goggle eyepiece of FIG. 5.

FIG. 7 illustrates a schematic side elevation view of the night vision goggle eyepiece of FIG. 5 showing the eye and scene imaging sensors located to one side of the goggles and substantially out of the user's field of vision.

In view of the foregoing description it will be evident to a person skilled in the art that various modifications may be made within the scope of the invention.

Each feature disclosed in the description, and (where appropriate) the claims and drawings may be provided independently or in any appropriate combination.

The scope of the present disclosure includes any novel feature or combination of features disclosed therein either explicitly or implicitly or any generalisation thereof irrespective of whether or not it relates to the claimed invention or mitigates any or all of the problems addressed by the present invention. The applicant hereby gives notice that new claims may be formulated to such features during the prosecution of this application or of any such further application derived there-from. In particular, with reference to the appended claims, features from dependent claims may be combined with those of the independent claims and features from respective independent claims may be combined in any appropriate manner and not merely in the specific combinations enumerated in the claims.

The invention claimed is:

1. An eye tracking apparatus for monitoring a movement of a user's eye, the apparatus comprising:
an optical assembly including: (i) an eye viewing element adapted to directly image a user's eye from within the user's field of vision, and (ii) an eye imaging sensor adapted to receive an image of the user's eye from said eye viewing element and provide an output indicative of the user's point of regard in the user's field of vision, said optical assembly including a first imaging path between said eye viewing element and said eye imaging sensor;
a scene viewing element adapted to image a scene served by the user's eye;
a scene imaging sensor adapted to receive an image of the scene from said scene viewing element via a second imaging path;
at least one infrared light emitting diode configured to illuminate the eye, in use; and
a processor programmed to temporally modulate an intensity of the at least one infrared light emitting diode when the eye tracking apparatus is operated in conjunction with an active secondary optical apparatus.

2. The eye tracking apparatus according to claim 1, wherein the optical assembly includes at least one relay lens adapted to provide a conjugate image of at least one of the user's eye and the scene being observed at an intermediate plane within the optical assembly so as to elongate at least one of the first and second optical paths.

3. The eye tracking apparatus according to claim 2, wherein the optical assembly includes:
said scene viewing element, said scene imaging sensor and the second optical path,
the eye imaging sensor is arranged remotely to the eye viewing element, the scene imaging sensor is arranged remotely to the scene viewing element, and
the optical assembly includes an optical combiner arranged to align at least a portion of the first and second optical paths coaxially along a common optical path.

4. The eye tracking apparatus according to claim 3, wherein the eye viewing element is arranged within 10-20 mm of the scene viewing element within the optical assembly.

5. The eye tracking apparatus according to claim 1, wherein the eye imaging sensor is adapted to image an object plane proximal to the eye viewing element and the scene imaging sensor is adapted to image an object plane distal to the scene viewing element, preferably at infinity.

6. The eye tracking apparatus according to claim 1, wherein the eye viewing element is substantially reflective to electromagnetic radiation.

7. The eye tracking apparatus according to claim 6, wherein the eye viewing element includes a plane mirror.

8. The eye tracking apparatus according to claim 1, wherein the eye viewing element is disposed in use within the user's lower field of vision in a region substantially 10-20 degrees below the user's straight ahead gaze.

9. The eye tracking apparatus according to claim 1, further comprising:
a video image recorder for recording the output from the eye imaging sensor indicative of the user's point of regard in the user's field of vision and an output from the scene imaging sensor.

10. The eye tracking apparatus according to claim 9, wherein the video image recorder is arranged to alternately record an output from the eye imaging sensor and the output from the scene imaging sensor.

11. The eye tracking apparatus according to claim 1, further comprising:
a processor adapted to determine the user's absolute point of regard in the user's field of vision.

12. The eye tracking apparatus according to claim 11, further comprising:
a display for displaying the user's absolute point of regard with respect to an image of the scene being observed by the user's eye.

13. An optical apparatus comprising:
at least one of spectacles, goggles, electro-optic goggles, night-vision goggles, virtual reality goggles, augmented reality goggles, a microscope, a telescope, binoculars and a head-mounted display, which includes an eye tracking apparatus according to claim 1.

14. The optical apparatus according to claim 13, further comprising an eyepiece, wherein the optical assembly extends at least partially across the front of said eyepiece.

15. The optical apparatus according to claim 14, wherein the optical assembly obscures substantially less than or equal to 15%, 10% or 5% of the optically transmissive area of the eyepiece.

16. A method of monitoring a movement of a user's eye, the method comprising the steps of:
(a) illuminating the user's eye with an infrared light emitting diode;
(b) capturing an image of the user's eye from a first position within the user's field of vision and relaying said image along a first optical path to a remote eye imaging sensor arranged out of the user's field of vision, (c) capturing an image of a scene being observed by the user's eye from a second position and relaying said image along a second optical path to a scene imaging sensor arranged out of the user's field of vision, and (d) temporally modulating the infrared light emitting diode when the eye tracking apparatus is operated in conjunction with an active secondary apparatus, wherein the images of the user's eye and scene are captured at substantially the same time.

17. The method of monitoring the movement of the user's eye according to claim 16, comprising the additional step of:

(e) providing an output indicative of the user's point of regard in the user's field of vision.

18. The method of monitoring the movement of the user's eye according to claim 16, wherein the second position is within the user's field of vision.

19. The method of monitoring the movement of the user's eye according to claim 16, wherein at least a portion of the first and second optical paths are coaxially aligned along a common optical path.

20. An eye tracking apparatus for monitoring a movement of a user's eye, the apparatus comprising:

an optical assembly including: (i) an eye viewing element adapted to directly image a user's eye from within the user's field of vision, and (ii) an eye imaging sensor adapted to receive an image of the user's eye from said eye viewing element and provide an output indicative of the user's point of regard in the user's field of vision, said optical assembly including a first imaging path between said eye viewing element and said eye imaging sensor;

a scene viewing element adapted to image a scene observed by the user's eye;

a scene imaging sensor adapted to receive an image of the scene from said scene viewing element via a second imaging path;

at least one infrared light emitting diode configured to illuminate the eye, in use; and means for temporally modulating an intensity of the at least one infrared light emitting diode when the eye tracking apparatus is operated in conjunction with an active secondary optical apparatus.

* * * * *